United States Patent [19]

Shih et al.

[11] Patent Number: 5,589,332

[45] Date of Patent: Dec. 31, 1996

[54] RIBOZYME AMPLIFIED DIAGNOSTICS

[75] Inventors: Andy Shih; Jeffrey M. Bockman; Shaji T. George, all of New York, N.Y.

[73] Assignee: Innovir Laboratories, Inc., New York, N.Y.

[21] Appl. No.: 240,081

[22] Filed: May 9, 1994

Related U.S. Application Data

[63] Continuation of Ser. No. 985,308, Dec. 4, 1992, abandoned.

[51] Int. Cl.$^6$ .............................. C12Q 1/68; C07H 21/02; C07H 21/04
[52] U.S. Cl. ................... 435/6; 536/24.5; 536/23.1
[58] Field of Search .................. 435/6, 91.2; 536/24.5, 536/23.1

[56] References Cited

U.S. PATENT DOCUMENTS 4,775,619  10/1988  Urdea ......................................... 435/6

FOREIGN PATENT DOCUMENTS

WO89/05852  6/1989  WIPO .

OTHER PUBLICATIONS

Noller, H. F., et al., "Unusual Resistance of peptidyl Transferase to Protein Extraction Procedures," *Science*, 256:1416–1419 (1992).

Altman, S., "Ribonuclease P: An Enzyme With a Catalytic RNA Subunit," in *Adv. Enzymol.*, 62:1–36 (John Wiley & Sons, New York, 1989).

Beaudry, A., et al.,G., "Directed Evolution of an RNA Enzyme," *Science*, 257:635–641 (1992).

Bock, L. et al., "Selection of Single–Stranded DNA Molecules that Bind and Inhibit Human Thrombin," *Nature*, 355.564–566 (1992).

Branch, A. et al., "The Brotherhood of Circular RNA Pathogens: Viroids, Circular Satellites, and the Delta Agent," *Semin. Virol.*, 1:143–152 (1990).

Brown, J. et al., "Characterization of RNAs from Thermophilic Bacteria," in Keystone RNA Processing Meeting, 55abs (Keystone, 1992).

Cech, T., "Ribozymes, Tools for Sequence–Specific Cleavage of RNA," *Editorial Comments*, 16:1–5 (U.S. Biochemicals Corp., Cleveland, 1989).

Ellington, A. D., et al., *Nature*, "In Vitro Selection of RNA Molecules that Bind Specific Ligands," 346:818–822 (1990).

(List continued on next page.)

*Primary Examiner*—W. Gary Jones
*Assistant Examiner*—Ethan Whisenant
*Attorney, Agent, or Firm*—Patrea L. Pabst

[57] ABSTRACT

A system is described for the use of a ribozyme as a diagnostic tool for detecting the presence of a nucleic acid, protein, or other molecule, in which the formation of an active ribozyme and cleavage of an assayable marker is dependent on the presence or absence of the specific target molecule. The essential component is a ribozyme specifically but reversibly binding a selected target in combination with a labelled co-target, preferably immobilized on a support structure. When both the target and co-target are bound, the ribozyme cleaves the label from the co-target, which is then quantifiable. Since the ribozyme is reversibly bound by target and co-target, it can reassociate with additional co-target, cleaving more label, thereby amplifying the reaction signal. In one embodiment, the target is a nucleic acid hybridizing to complementary sequences that form part of the ribozyme; in a second embodiment, the target is a protein or other macromolecule which is bound by interactions with a portion of the ribozyme molecule in another embodiment, a thermostable ribozyme is used, so that improperly bound ribozyme is destabilized and inactive at elevated temperatures. A method for isolating regularable ribozymes is also disclosed. The regulatable ribozymes are useful in the method for detecting the presence of a specific macromolecule, or can be used in in vitro or in vivo methods for inactivation or activation of the cleavage of target RNA molecules.

25 Claims, 9 Drawing Sheets

OTHER PUBLICATIONS

Ellington, A. D., et al., "Selection In Vitro of Single-stranded DNA Molecules that Fold into Specific Ligand-binding Structures," *Nature*, 355:850–852 (1992).

Forster, A. C., et al., "External Guide Sequences for an RNA Enzyme," *Science*, 249:783–786 (1990).

George, S. T., et al., "Robozyme Accessibility of Potential Cleavage Sites in Hepatitis B Virus S Gene Messenger RNA," *Abstracts: Molecular Biology of Hepatitis B Viruses*, 131 (La Julia, CA, 1992).

Haseloff, J., et al., "Simple RNA Enzymes with New and Highly Specific Endoribunuclease Activities," *Nature*, 334:585–591 (1988).

Herschlag, D., et al., "DNA Cleavage Catalysed by the Ribozyme from *Tetrahymena*," *Nature*, 344:405–409 (1990).

Kuo, M. Y. -P.,et al., "Characterization of Self-Cleaving RNA Sequences on the Genome and Antigenome of Human Hepatitis Delta Virus," *Journal of Virology*, 62(12):4439–4444 (1988).

Perotta, A. T., et al., "The Self-cleaving Domain from the Genomic RNA of Hepatitis Delta Virus: Sequence Requirements and the Effects of Denaturant," *Nucleic Acids Res.*, 18(23):6821–6827 (1990).

Perotta, A. T., et al., "A Pseudoknot-like Structure Required for Efficient Self-cleavage of hepatitis Delta Virus RNA," *Nature*, 350:434–436 (1991).

Perotta, A. T., et al., "Cleavage of Oligoribunucleotides by a Ribozyme Derived from the Hepatitis δ Virus RNA Sequence," *Biochemistry*, 31:16–21 (1992).

Piccirilli, J. A., et al., "Aminoacyl Esterase Activity of the Tetrahymena Ribozyme," *Science*, 256:1420–1424 (1992).

Robertson, D., et al., "Selection In Vitro of an RNA Enzyme that Specifically Cleaves Single-stranded DNA," *Nature*, 344:467–469 (1990).

Rosenstein, S.P., et al., "Self-cleavage of hepatitis Delta Virus Genomic Strand RNA is Enchanced under Partially Denaturing Conditions," *Biochemistry*, 29:8011–8016 (1990).

Sharmeen et al., "Antigenomic RNA of Human Hepatitis Delta Virus Can Underto Self-cleavage," *J. Virol.*, 62:2674–2679 (1988).

Shih et al., "Efficient Trans-cleavage and Re-targeting of hepatitis Delta Virus Ribozymes," *Abstracts: Molecular Biology of Hepatitis B Viruses*, 130 (La Jolla, CA, 1992).

Smith, J. B., et al., "Antigenomic Hepatitis Delta Virus Ribozymes Self-cleave in 18 M Formamide," *Nucleic Acids Research*, 19(6):1285–1289 (1991).

Symons, R. H., et al., "Ribozymes," *Critical Reviews in Plant Sciences*, 10(3):189–234 (CRC Press, Inc. Boca Raton, Fla. 1991).

Szostak, J. W., "In Vitro Genetics," *Trends Biochem. Sci.*, 17:89–93 (1992).

Uhlenback, O. C., "A Small Catalytic Oligoribonucleotide," *Nature*, 328:596–600 (1987).

Weizsacker, F. von., et al., "Cleavage of hepatitis B Virus RNA by Three Ribozymes Transcribed from a Single DNA Template," *Biochem. Biophys. Res. Comm.*, 189(2):743–748 (1992).

Wu, H–N, et al., "Reversible Cleavage and Ligation of Hepatitis Delta Virus RNA," Science, 243:652–655 (1989).

Wu, H–N, et al., "RNA Conformational Requirements of Self-cleavage of Hepatitis Delta Virus RNA," *Mol. Cell. Biol.*, 10(10):5575–5579 (1990).

Wu, H–N, et al., "Human hepatitis δ Virus RNA Subfragments Contain an Autocleavage Activity," *Proc. Natl. Acad. Sci. USA*, 86:1831–1835 (1989).

Yuan, Y., et al., "Targeted Cleavage of mRNA by Human RNase P." *Proc. Natl. Acad. Sci. USA*, 89:8006–8010 (1992).

Zaug, A. J., et al., "The Intervening Sequence of RNA of *Tetrahymena* is an Enzyme," *Science*, 231:470–475 (1986).

Forester et al. Cell 49:211–220 (1987).

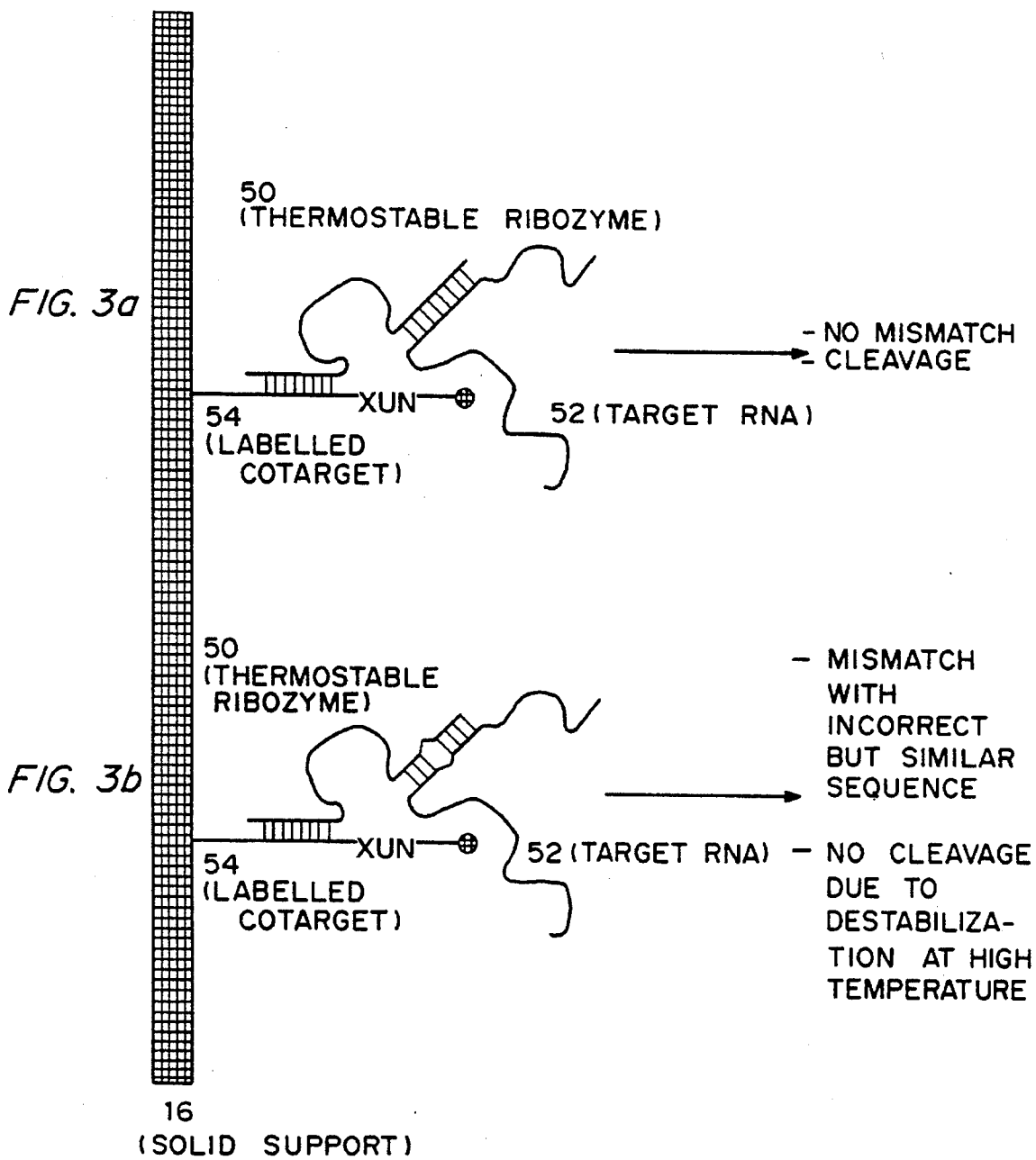

RIBOZYME AMPLIFIED DIAGNOSTICS

This is a continuation of U.S. patent application Ser. No. 07/985,308 filed on Dec. 4, 1992, (now abandoned).

BACKGROUND OF THE INVENTION

The present invention is a system for the design of diagnostics having an amplified or differential response as a result of the inclusion of a ribozyme.

The detection of infectious agents or molecules indicative of disease, including metabolites, nucleic acids, and proteins, is a fundamental component in the diagnosis and treatment of medical disorders, as well as in research. A number of methodologies are currently in use for detection. These methodologies can generally be divided into antibody-based diagnostic assays for proteins, either components of the disease causing agent or byproducts of the disease, and diagnostic assays for nucleic acids, such as the genetic material encoding a component of the disease causing agent.

Assays for proteins are further divided into those methods which involve a binding reaction between a molecule (usually an antibody) and the protein to be detected, or a reaction between an enzyme which binds the targeted molecule resulting in activation of the enzyme so that it can cleave a substrate to produce a detectable color change. Many of the binding assays include a dye, an enzyme, or a radioactive or fluorescent label to enhance detection. Antibodies to the protein can be obtained from patients, immunized animals, or antigen-specific monoclonal cell lines. These antibody assays include assays such as sandwich ELISA assays, Western immunoblot, radioimmunoassays, and immunodiffusion assays. Other assays use molecules such as avidin and biotin for immobilization and detection of molecules. Techniques for preparing these reagents and methods for use thereof are known to those skilled in the art.

Assays for nucleic acid sequences range from simple methods for detection, such as a Northern blot hybridization using a radiolabeled probe to detect the presence of a nucleic acid molecule, to the use of the polymerase chain reaction (PCR) to amplify a very small quantity of a specific nucleic acid sequence to the point at which it can be used for detection of the sequence by hybridization techniques. Nucleotide probes can be labelled using dyes, or enzymatic, fluorescent, chemiluminescent, or radioactive labels which are commercially available. These probes can be used to detect by hybridization the expression of a gene or related sequences in cells or tissue samples in which the gene is a normal component, as well as to screen sera or tissue samples from humans suspected of having a disorder arising from infection with an organism, or to detect novel or altered genes as might be found in tumorigenic cells. Nucleic acid primers can also be prepared which, with reverse transcriptase or DNA polymerase and the polymerase chain reaction, can be used for detection of nucleic acid molecules which are present in very small amounts in tissues or fluids.

Only the enzyme-based methodologies and PCR (which uses a polymerase) are inherently catalytic, with detection linked to amplification of the signal. PCR has several disadvantages, although it is capable of detecting very small quantities of DNA: it requires a high degree of technical competence for reliability; it is extremely sensitive to contamination resulting in false positives; it is difficult to use quantitatively rather than qualitatively. The other methods rely on conjugation of an enzyme, usually to additional components of the assay, to increase signal generation and amplification. The use of these additional ligands increases the noise of the system, with higher background and false positives, and necessitates several levels of control reactions.

Ribozymes are defined as RNA molecules having enzyme like activity. There are three general pathways of RNA catalyzed cleavage: (1) cleavage by viroid-like RNA; (2) cleavage by RNAase P or the RNA component of RNAase P, the work of Sidney Altman at Yale University; and (3) cleavage by the *Tetrahymena* ribozyme, the work of Thomas Cech at the University of Colorado. All naturally occurring ribozymes known to date, with the exception of RNAase P, work in cis and must be engineered to work in trans, i.e., on another molecule. This is accomplished by separating the portion of the RNA molecule with enzymatic activity from the portion serving as substrate, and conferring substrate-like properties, including appropriate secondary and tertiary structure, on the target molecule which is to be cleaved. Specificity can be conferred by adding complementary nucleic acid sequence which hybridize adjacent to the site to be cleaved on the target molecule.

Each class of ribozyme cleaves a different sequence of nucleotides using distinct mechanisms of action. Moreover, each class is further distinguished based on how many nucleotide bases are essential for enzymatic activity and to the extent the intended target and the ribozyme can be manipulated to alter specificity.

The *Tetrahymena* ribozyme was the first ribozyme to be discovered. This ribozyme is guanosine-dependent for its cleavage. It is a large ribozyme that naturally operates in cis. A smaller internal portion can be engineered to operate in trans, that is, on a separate molecule, targeting specific four nucleotide sequences.

M1 RNA, the RNA ribozyme subunit of *E. coli* RNAase P, is a nearly 400-base RNA molecule which cleaves a whole variety of separate, other molecules in the cell to produce mature tRNAs from their precursors. Other molecules can be converted into substrate for M1 RNA through the use of an external guide sequence characterized as an isolated oligoribonucleotide having at its 5' terminus at least seven nucleotides complementary to the nucleotides 3' to the cleavage site in the RNA to be cleaved and at its 3' terminus the nucleotides N C C A directly joined to the complementary nucleotides, wherein N is any nucleotide and the complementary nucleotides in the oligoribonucleotide hybridizes to the complementary nucleotides in the RNA to be cleaved, as described by Forster and Altman, in *Science* 249:783–786 (1990), "External Guide Sequences for an RNA Enzyme". Altman, et al., *Proc. Natl. Acad. Sci.* 89 (17):8006–8010 (1992), "Targeted Cleavage of Messenger RNA by Human RNase P" recently described the construction of an external guide sequence for the eukaryotic equivalent of the *E. coli* RNAase P, based on a structure derived from a precursor TRNA. The RNAase P reaction and the *Tetrahymena* reaction both act by creating 5'-phosphate and 3'-hydroxyl termini.

There are several kinds of viroid-like RNA ribozymes found in plants and animals. The hammerhead ribozyme is one class in this category and the hepatitis delta ribozyme is a second class. Unlike the RNAase P and Tetrahymena ribozymes, the engineered trans-acting plant viroid-like ribozymes are only 18 to 20 nucleotide bases long with equally short substrates. The central motif is a characteristic conserved sequence motif that Uhlenbeck demonstrated in 1987 and published in Nature 328:596–600 (1987), in which he proposed that all hammerheads shared certain features. The cleavage reaction of the viroid-like ribozymes creates a 2', 3' cyclic phosphate and a 5' hydroxyl terminus. Accordingly, there is a fundamentally and mechanistically different chemistry for these viroid-like RNA reactions as contrasted with the M1 RNA reaction or the *Tetrahymena* reaction. However, the end result is the same, i.e., cleavage of a separate RNA molecule.

It has been proposed by several groups that ribozymes have the potential to be used to treat disease or genetic disorders by cleaving target RNA, such as viral RNA or MRNA transcribed from genes which should be, but are not, turned off. No one has proposed using them as diagnostics, however.

It is therefore an object of the present invention to provide a means for amplification or generation of a diagnostic response using ribozymes.

It is a further object of the present invention to utilize ribozymes to serve as a catalyst in the detection of nucleic acids, proteins, and other molecules, in which detection is a result of cleavage of a substrate by the ribozyme.

SUMMARY OF THE INVENTION

A system is described for the use of a ribozyme as a diagnostic tool for detecting the presence of a nucleic acid, protein, or other molecules, in which the formation of an active ribozyme and cleavage of an assayable marker is dependent on the presence of the specific target molecule. The essential component is a ribozyme specifically but reversibly binding a selected target in combination with a labelled co-target, preferably immobilized on a support structure. When both the target and co-target are bound, the ribozyme cleaves the label from the co-target, which is then quantifiable. Since the ribozyme is reversibly bound by target and co-target, it can reassociate with additional co-target, cleaving more label, thereby amplifying the reaction signal. In one embodiment, the target is a nucleic acid hybridizing to complementary sequences that form part of the ribozyme; in a second embodiment, the target is a protein or other macromolecule which is bound by interactions with a portion of the ribozyme molecule. In still another embodiment, a thermostable ribozyme is used, so that improperly bound ribozyme is destabilized and inactive at elevated temperatures.

A method for isolating regulatable ribozymes is also described. The regulatable ribozymes are useful in the method for detecting the presence of a specific macromolecule, or can be used in in vitro or in vivo as methods for inactivation or activation of cleavage of target RNA molecules.

BRIEF DESCRIPTION OF THE DRAWINGS

FIG. 2A is when the ribozyme is bound to ligand and in an active conformation; FIG. 2B is when the ribozyme is not bound to ligand and is in an inactive conformation.

FIGS. 3A and 3B are schematics of a thermostable ribozyme amplified diagnostic system, where the ribozyme which is properly matched with target and co-target and conformationally active is shown in FIG. 3A and the ribozyme which is destabilized and conformationally inactive is shown in FIG. 3B.

DETAILED DESCRIPTION OF THE INVENTION

A ribozyme-based diagnostic method has several advantages over existing diagnostic methods. The method combines highly specific ligand interactions with inherently catalytic properties, and is therefore simple, sensitive, and can be quantitative. The specificity depends not only on specific complementarity between the ribozyme arms and the target RNA but also on the presence and correct spatial orientation of the cleavage recognition site, for example, the triplet (NUX). In addition, while ribozymes seem primarily to interact with other RNA molecules, recent work shows that RNA and DNA can be selected in vitro to bind or catalyze a reaction on other molecules, including drugs and metabolites, or macromolecules, including nucleic acids and proteins. See, Joyce, *Gene* 82:83, 1989; Robertson and Joyce, *Nature* 344:467, 1990; Ellington and Szostak, *Nature* 346:818, 1990; Piccirilli, et al., *Science* 256:1420, 1992; Noller, et al., *Science* 256:1416, 1992; Ellington and Szostak, *Nature* 355:850, 1992; Bock, et al., *Nature* 355:564 1992, the teachings of which are specifically incorporated herein.

The ribozyme diagnostic system utilizes the ability to separate a unimolecular, cis-acting ribozyme into a bi- or trimolecular trans-acting system: in the bimolecular system, an active ribozyme is formed by the complex of ribozyme molecule and disease target molecule, with the cleavage site located in the ribozyme molecule; or in the trimolecular system, an active ribozyme is formed by the complex of ribozyme molecule, a co-target molecule which contains the cleavage site, and the disease target molecule.

Method for Ribozyme Amplified Diagnostic Detection.

Figure 1A:
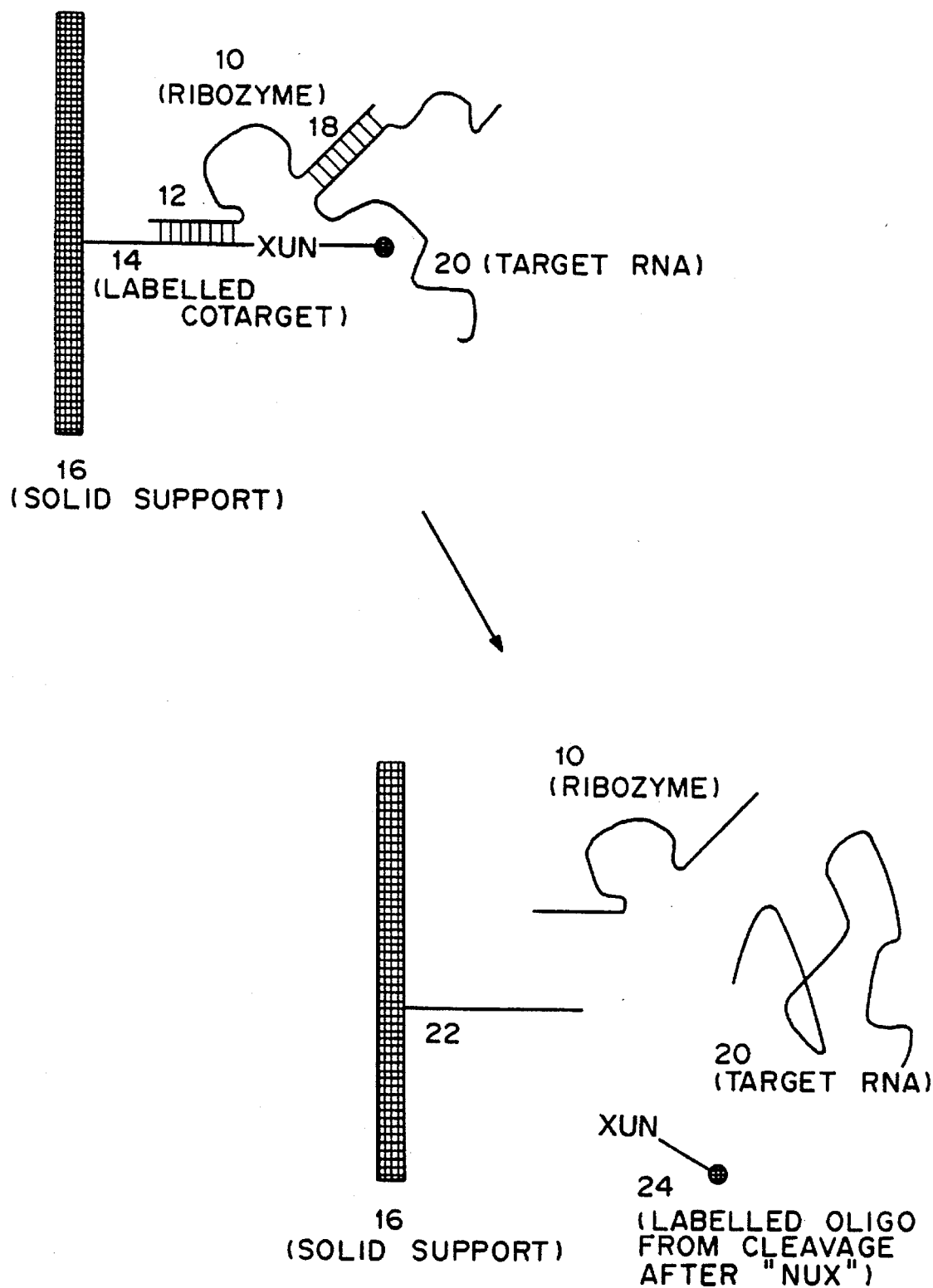
FIGS. 1A, 1B, and 1C are schematics of the ribozyme amplified diagnostic components, a ribozyme with one arm designed to base-pair with labelled RNA molecules bearing a labelled NUX cleavage site, which are anchored to a solid support, referred to as the "co-target" RNA, and the other arm designed to base-pair with a predetermined sequence on the RNA being detected, the "target" RNA.

As depicted in FIG. 1A, the ribozyme amplified diagnostic (RAD) methodology includes three principal components: a ribozyme 10, with one arm 12 designed to base-pair with labelled RNA molecules 14 bearing an NUX cleavage site and referred to as the "co-target" which are anchored to a solid support 16, and the other arm 18 of ribozyme to base-pair with a predetermined sequence on the RNA being detected, the "target" RNA 20.

When the ribozyme 10 cleaves the co-target RNA 14, the portion 22 of the co-target remains bound to support 16 and the labelled NUX-bearing portion 24 is released. Release of label from an unknown sample allows the determination of the approximate number of target molecules present; i.e., by constructing a standard curve of the cleavage of the co-target in the presence of varying amounts of target, one can determine the approximate number of target molecules present in the sample.

Figure 1B:
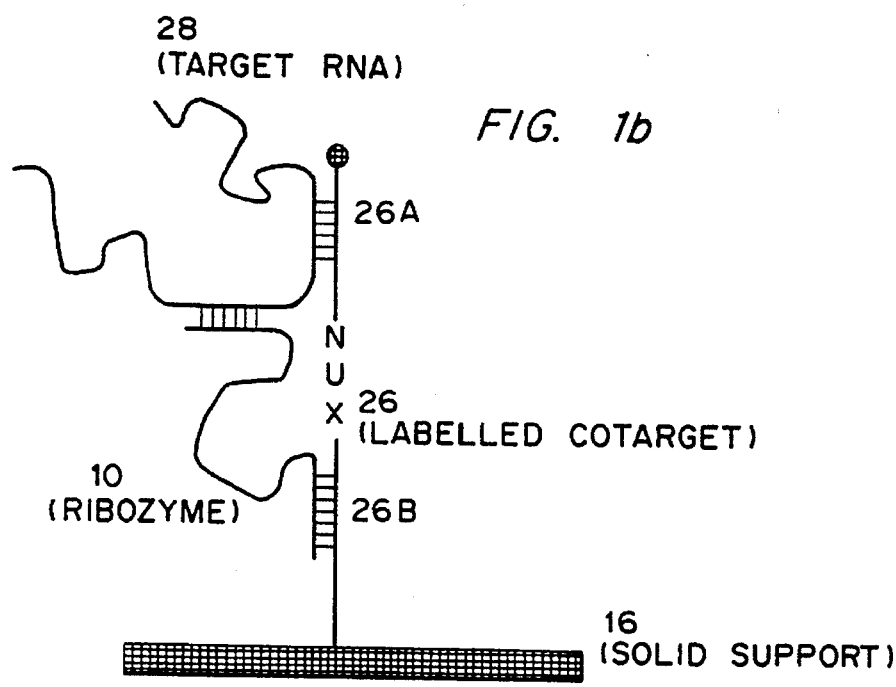

In the variation seen in FIG. 1B, three base-pairings are involved, one at 26b between the ribozyme 10 and the cotarget 26 bound to the support 16, one between the ribozyme 10 and the target 28, and one at 26a between the co-target 26 and the target 28. Only when the target RNA 28 is present and bound by the ribozyme 10 and the co-target 26 does the catalytically active ribozyme conformation form. The active trimolecular complex of ribozyme 10, co-target 26 and target 28 results in cleavage of the labelled co-target 26 at the NUX site and the release of a labelled oligonucleotide 26a from the solid support 16 into solution, where it is assayed. Since the base-pairing is reversible, the ribozyme 10, cleaved co-target 26 and target 28 are free to dissociate from each other and form a new active complex between ribozyme, a new molecule of uncleaved co-target, and target molecules. This recycling amplifies the release of the label and hence the signal, leading to the high sensitivity of the system and a low level of false negatives. The high specificity of the system results in a low level of false positives.

Figure 1C:
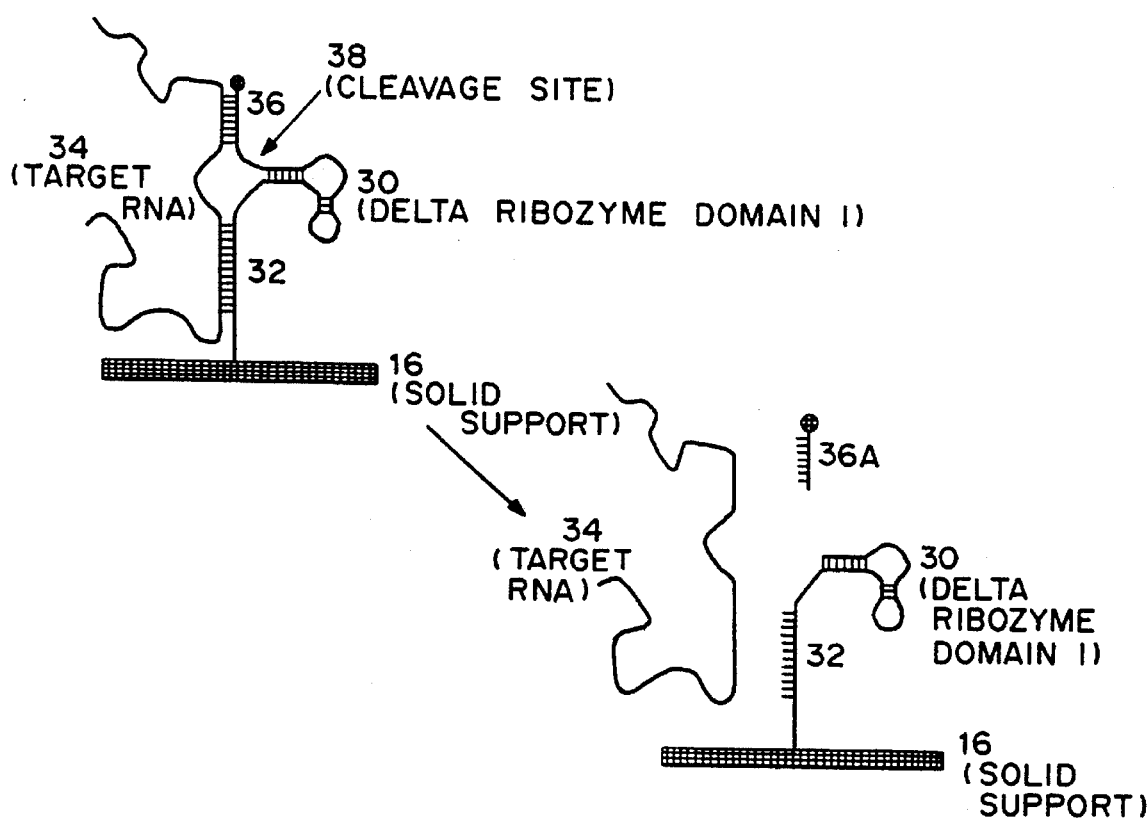

A further variation of the method is depicted in FIG. 1C. It has been shown that an engineered ribozyme derived from hepatitis delta virus can be separated into two subdomains which when reconstituted reform an active ribozyme structure with resultant cleavage of one of the domains (Branch and Robertson, *Proc. Natl. Acad. Sci.* 88:10163 (1991), the teachings of which are incorporated herein). The delta ribozyme can be retargeted by replacing designated sequences in domain I with sequences 32 and 36 complementary to a chosen sequence in a target RNA 34. The retargeted domain I 30 remains inert unless complexed with the proper target RNA 34 to reconstitute an active conformation of the ribozyme 30, resulting in cleavage at the designated site 38.

When ribozyme domain I 30 is anchored to a solid support 16 and labelled with a detectable label such as a radioactive label, a fluorescent label, a dye, a chemiluminescent label or an enzyme reactive with a chromogenic substrate, it can be used to determine the presence of target RNA 34 present in a clinical sample. The active ribozyme conformation will form following binding of the target RNA 34, resulting in the cleavage and release of a labelled oligonucleotide 36a. This method is not only applicable to the delta ribozyme but to any ribozyme which can be separated in an analogous fashion.

The reactions can be carried out in standard reaction vessels for assays such as microtiter well plates. In a preferred embodiment, the solid substrate will be the walls of the microtiter plates, microbeads, or other inert materials commonly used in diagnostic assays. Methods for immobilization are known to those skilled in the art, for example, in *Nature* 357:519–520 (1992), the teachings of which are incorporated herein.

Figure 2A:
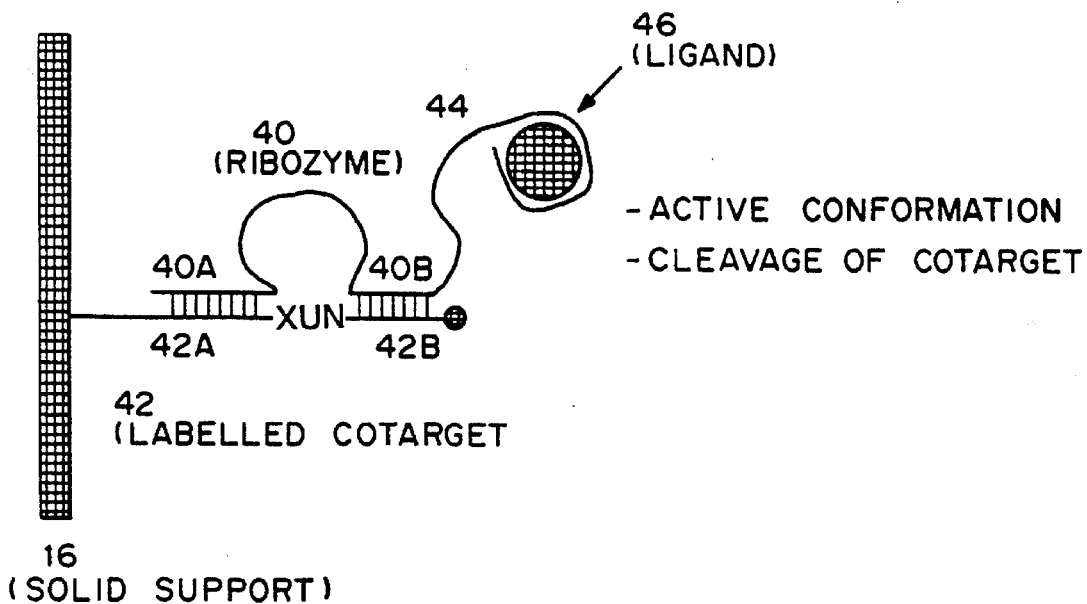
FIGS. 2A and 2B are schematics of the ribozyme amplified diagnostic components for detection of a non-nucleic acid molecule, a ribozyme that forms an enzymatically active conformation when a ligand binding portion binds to ligand which is to be detected and a co-target molecule which is cleaved by the active ribozyme to release a detectable labelled sequence.
Figure 2B:
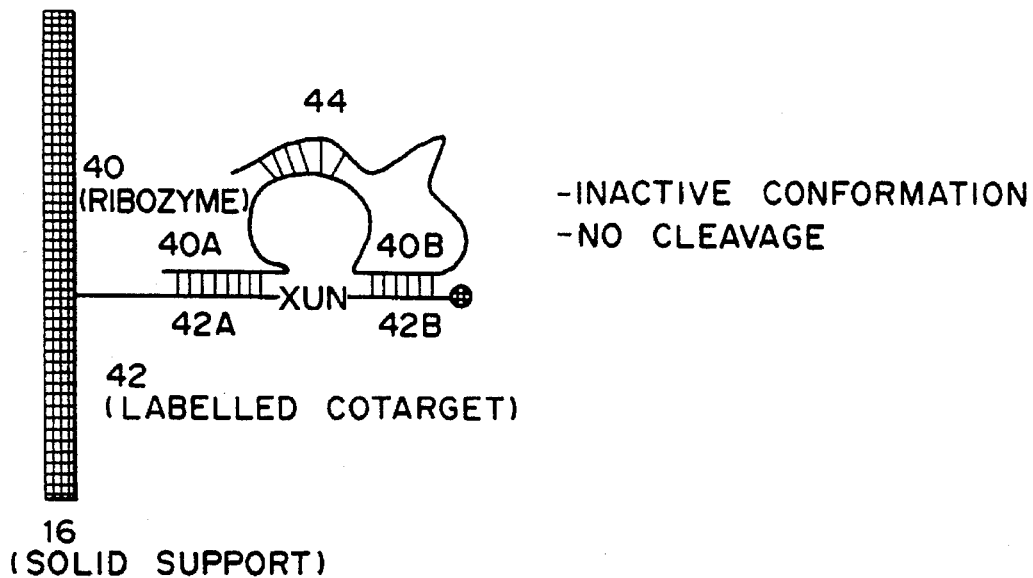

The methodology above can be modified to allow detection of pathogenic molecules or macromolecules other than nucleic acid, such as proteins, as shown in FIG. 2. Referring to FIG. 2A, a ribozyme sequence 40, which is directed entirely against an engineered co-target 42 (that is, both arms 40a and 40b of the ribozyme are complementary to the co-target 42a and 42b), is constructed. The ribozyme 40 is then linked to sequences 44 which have been selected to both bind a non-nucleic acid ligand 46, such as a protein, and, when bound, to place the entire sequence of ribozyme 40 plus ligand binding region 44 into a conformation in which the ribozyme is active. One can then use activation of the ribozyme to cleave co-target 42 to release oligonucleotide 42b which is labelled and which can be detected; release of label is indicative of the presence of the given ligand 46. This regulatable ribozyme 40 binds reversibly to cotarget 42, and can therefore continue to interact with uncleaved co-targets, resulting in amplification of the signal. The inactive conformation of ribozyme 40 is shown in FIG. 2B, where the ligand binding sequence 44 is folded back on the ribozyme 40, which is in an inactive conformation and unable to cleave cotarget 42.

In order to increase the rate of catalysis of the methodologies depicted in FIGS. 1 and 2, and/or to increase the specificity of the reaction, one can use a more thermostable ribozyme isolated from thermophilic organisms (Brown et al, *Keystone RNA Processing Meeting*, Keystone, p55abs, 1992) or selected using "in vitro genetics" (Szostak, *TIBS* 17:89, 1992) in order to carry out the above methods at higher temperatures. Thermostable RNase P from *thermus aquaticus* and *thermotoga maritima* can also be used. At higher reaction temperatures, mismatches between the ribozyme guide sequences and the target will be thermodynamically unfavorable for formation of a stable and active complex; i.e., the arms will not remain hybridized relative to targets with exact complementarity. Thus, a ribozyme whose catalytic core remains conformationally active at the elevated temperature will be able to discriminate between the target and any possibly partially homologous non-target sequences. At standard reaction temperatures, protypical ribozymes would be unable to make as stringent a distinction, binding with essentially identical kinetics to similar but non-identical sequences, for example, two mismatches out of ten. This is analogous to the identification of single base pair mismatches by standard hybridization probe technology or with PCR.

For *in vitro* selection, one applies the methodology described above for *in vitro* genetics to generate a population of ribozymes with random genetic variations in the sequence of a ribozyme functioning optimally at 37° C. One then assays and selects for those ribozymes functioning efficiently at elevated temperatures. See, for example Beaudry and Joyce, *Science* 257:635–641 (1992), the teachings of which are incorporated herein. The gene product can be selected, for example, by its ability to bind a ligand or to carry out a chemical reaction. The gene that corresponds to the selected gene product, or a particular ribozyme, can be amplified by a reciprocal primer method, such as the polymerase chain reaction. Using a combination of two polymerase enzymes, virtually any RNA can be amplified. RNA is reverse transcribed to a complementary DNA (cDNA) with reverse transcriptase (RT), and the resulting cDNA is transcribed to RNA with T7 RNA polymerase. Amplification occurs during transcription as a consequence of the ability of the T7 polymerase to generate 200 to 1200 copies of RNA transcript per copy of cDNA template. The amplification is performed selectively in that individual RNAs in the population are required to catalyze a particular chemical reaction in order to become eligible for amplification. Selection is based on the ability of the ribozyme to catalyze a sequence-specific reaction involving an oligonucleotide or oligodeoxynucleotide substrate. The product of the reaction is a molecule that contains the 3' portion of the substrate attached to the 3' end of the ribozyme. Selection occurs when an oligodeoxynucleotide primer is hybridized across the ligation junction and used to initiate cDNA synthesis.

Mutations can be introduced by use of a set of mutagenic oligodeoxynucleotides that contain random substitutions at a fixed frequency of occurrence. These partially randomized oligonucleotides are produced on an automated DNA synthesizer with nucleoside 3'-phosphoramidite solutions containing a small percentage of incorrect monomers. After each round of selective amplification, random mutations are introduced by performing the PCR under mutagenic conditions. The RNAs obtained by selective amplification are subjected to reverse transcription, the resulting cDNAs are PCR amplified, and the PCR products are transcribed to produce a progeny distribution of mutant RNAs.

As shown in FIG. 3A, the thermostable ribozyme 50 is specific for target 52 and co-target 54 at elevated temperatures, for example, 60° C. versus 45° C. The temperature will vary for each ribozyme system, for example, hammerheads, RNase P, or HDV ribozymes. A mismatch as shown in FIG. 3B does not result in cleavage when the temperature is elevated to greater than 37° C., ie., 45° to 60° C.

In summary, the disclosed methodology is highly specific due to the multiple requirements for ribozyme cleavage to occur; it is highly sensitive due to the inherent catalytic properties of the ribozyme which allow for amplification of the signal; the system is easily modified to target any RNA molecule (only one arm of the ribozyme need be altered in its sequence), requiring only resynthesis of the ribozyme; it is easily amenable to pre-existing hardware such as microtiter plate readers; it is logistically simple and rapid, requiring a few components which interact simultaneously rather than sequentially; and lastly, it is easily quantifiable.

Ribozymes

A variety of ribozymes can be utilized in the methods described above. The selection of ribozyme determines the specificity of cleavage and the immobilized co-target must be designed accordingly. The ribozyme activity can be controlled by a change in conformation of the ribozyme effected by binding to the target and/or co-target, or by the construction of a ribozyme which can bind a non-nucleic acid ligand, as well as the cotarget. This ribozyme, in the absence of the ligand, cannot bind the cotarget, because the conformation of the ribozyme sterically blocks binding; or binds but cannot cleave because the ribozyme remains in an inactive conformation. When the ligand is present, the ribozyme binds to it in such a way that the ribozyme can now bind to the cotarget, assume an active conformation, and cleave the target.

Ribozymes that can be regulated can be prepared and isolated by the method described below. Appropriate oligonucleotides are synthesized on an Applied Biosystems Incorporated (ABI, 850 Lincoln Center Dr., Foster City, Calif. 94404) Model 392 synthesizer using company reagents. The general design criteria are described above with reference to the figures. These are all subject to modifications and variations which do not alter the functionality of the ribozymes.

Figure 4A:
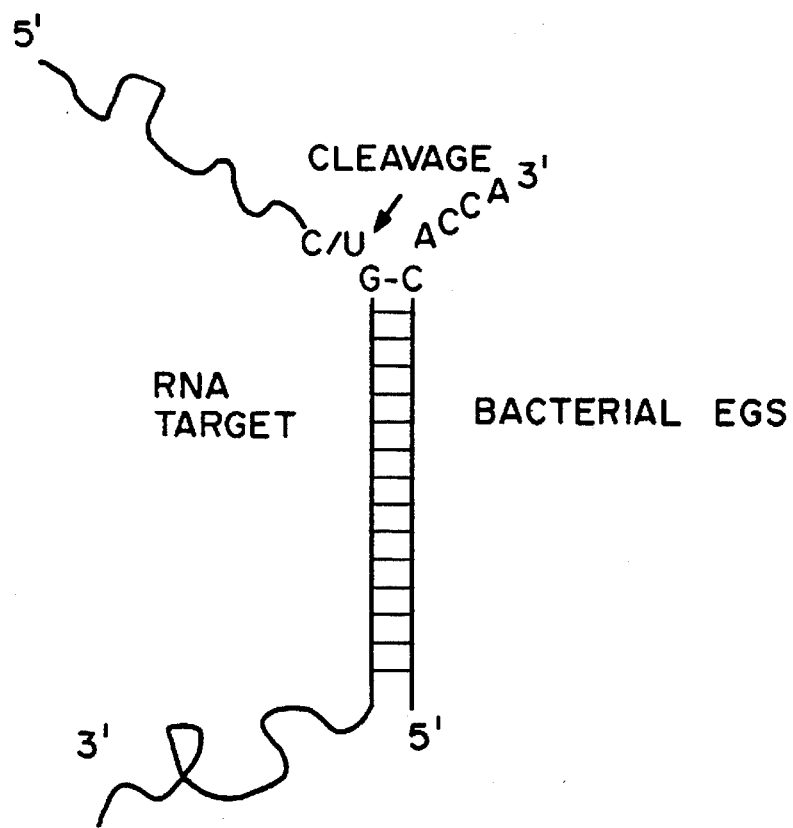
FIGS. 4A and 4B are schematics of the cleavage of a target using RNAase P in combination with an appropriate EGS to guide either bacterial RNAase P (FIG. 4A) or human RNAase P (FIG. 4B).
Figure 4B:
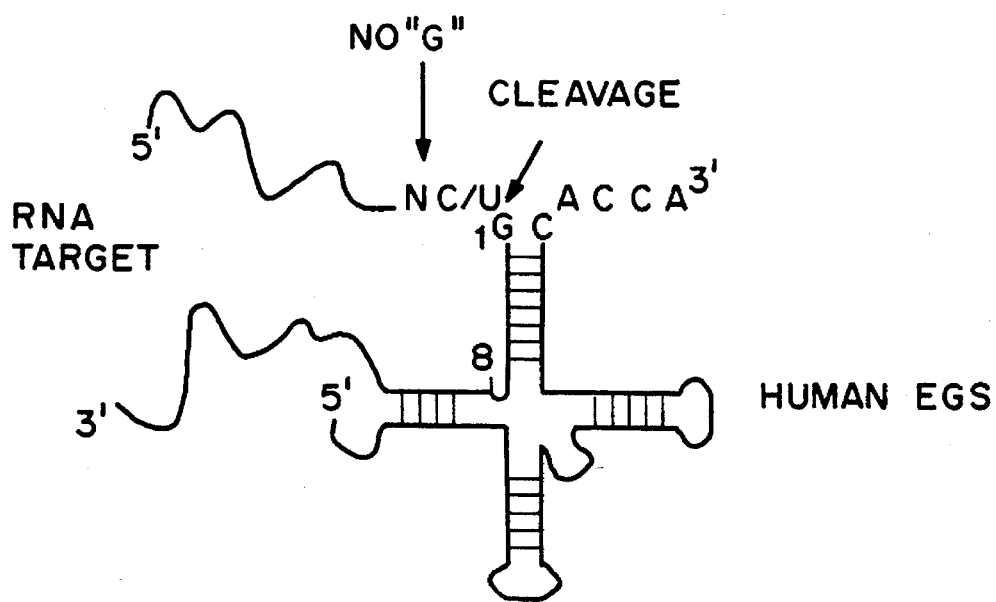

The site of cleavage of the co-target molecule is dependent on the selection of the ribozyme system. The sequence to be cleaved is dependent on the selection of the ribozyme. For example, if the ribozyme is derived from newt satellite RNA, the cleavage site follows NUX, where N=any nucleotide, X=any nucleotide except G, and U is uridine. For RNase P, the known sequence-specific requirements are shown in FIG. 4A and 4B (bacterial and eukaryotic RNAase P, respectively). No selection criteria are necessary for the cleavage site, since this resides in the cotarget, which is derived from the known cis-cleaving ribozyme sequence; the strategy of the method described herein is to always separate the ribozyme system in such a way as to place the cleavage site sequence requirements entirely in the cotarget, so that the only requirement for interaction between the ribozyme/cotarget and the disease target is some stretch of complementary nucleotides, without any specific sequence requirements.

There is no set number of base pairs for hybridization; the length of base pairs between ribozyme and target, ribozyme and co-target, and co-target and target, will vary with each ribozyme system and particular diagnostic situation. For example, the salt and temperature, or other reaction conditions, will be empirically optimized for each case in order to maximize the signal-to-noise ratio.

Selection of target RNAs and Co-target RNAs

Any RNA molecule can be targeted for use with the method. Preferred RNA molecules are those for which at least partial sequence is known so that complementary sequence can be made to bind the ribozyme sequence to both the target and cotarget molecules. Examples of targeted molecules include mRNAs encoding proteins, especially proteins characteristic of a particular condition, disorder, or disease, or derived from a pathogenic agent, and RNAs encoding viral proteins or RNA genomes. Examples of targeted RNAs include endogenous RNAs, either mRNAs encoding proteins or other non-coding RNAs, which are involved in the pathogenesis of a particular disorder, condition, or disease, or exogenous RNAs which exist inside or outside of the cell but are derived from pathogenic agents such as viruses, bacteria, fungi, etc, which are involved directly or indirectly in a disease state. Examples of targeted non-nucleic acid molecules include proteins, such as tumor-specific or oncogenic proteins, such as mutant ras; hormones, such as human chorionic gonadotropin; metabolites indicative of drug use; and toxins that are identified in environmental or forensic testing.

Regulation of Ribozyme Activity

The methodology for the construction of a regulatable ribozyme, in which a ribozyme sequence is linked to a ligand-binding sequence, placing the activity of the ribozyme under the control of that ligand and requiring its presence for activation or inactivation, is described below. DNA oligonucleotides are synthesized which contain the T7 promoter and the sequence coding for a given ribozyme preceded by or followed by a random sequence of length n. The resulting DNA is a mixture of molecules (of complexity $4^n$). Transcription in vitro by T7 RNA polymerase generates a complex pool of RNA molecules, each one having the defined ribozyme sequence linked to a random sequence of length n. Although the ribozyme sequence is defined, the conformation of the entire molecule, including that portion corresponding to the ribozyme, is determined by the interaction of the random sequence with itself and the ribozyme sequence. To select for those molecules which fold into a conformation which binds the desired ligand, preferably a small organic molecule of sufficient complexity to allow binding, or a macromolecule such as a protein, the complex pool of RNA molecules is subjected to repeated rounds of affinity chromatography in which the ligand is covalently bound to the matrix and those RNA molecules which bind remain on the column until specifically eluted. The eluted, ligand-binding RNAs are amplified using the polymerase chain reaction (PCR) in order to enrich for the ligand-binding molecules. PCR reagents and methodology are available from Perkin Elmer, 761 Main Ave., Norwalk, Conn. 06850; or Roche Molecular Systems, 1145 Atlantic Ave., Suite 100, Alameda, Calif. 94501. After several such cycles a population of RNA results in which virtually every molecule can bind the ligand.

A certain number of molecules should fold in such a way as to inactivate the ribozyme by sterically hindering the ability of the arms of the ribozyme portion of the molecule to bind to the target RNA and/or so as to alter the conformation of the catalytic core of the ribozyme, inhibiting cleavage, but fold in such a way that subsequent binding of the co-ligand activates the ribozyme. Examples of ligands include proteins such as those defined above as targets. Alternatively, a certain number of molecules should fold into the inactive conformation only in the presence of the ligand, and in its absence fold into a catalytically active conformation.

The population of ligand-binding RNAs is then screened for activation or inactivation of the ribozyme by the co-drug ligand. The selection can be accomplished in at least two ways. In the first, the pure population of ligand-binding RNA molecules is converted to double-stranded DNA via reverse transcriptase and then cloned into an in vitro expression vector. Individual bacterial transformants bearing a cloned sequence are grown up, the recombinant plasmid purified and the gene encoding the ligand-binding/ribozyme RNA transcribed. The homogeneous RNA from each clone is then assayed for cleavage in the presence or absence of the ligand. Alternatively, a strategy for logistically simplifying the screening, reducing the total number of clones which must be isolated and transcribed and assayed, can be employed. One such method is to perform limiting dilution of the complex pool of ligand-binding molecules. From the concentration of RNA and the known size of the molecules, the number of molecules per unit volume, the molarity of the RNA solution, can be easily determined. Dilutions of the RNA would be made to statistically favor, for example, 10 RNA molecules per assay well. In 100 microtiter plates (96 well), approximately $10^5$ molecules could be assayed for cleavage. Ellington and Szostak (1990) estimated there would be 1 in $10^{10}$ RNA molecules folded in such a way as to bind a given ligand in the original population of $10^{15}$ different sequences and that there were $10^2$ to $10^3$ different sequences in the final preparation. After purification for ligand-binding, virtually 100% of the molecules bind ligand. If only one molecule out of the $10^5$ different ligand-binding molecules had the ribozyme activated or inactivated by the presence of ligand, this scheme would allow for its isolation. Because the ligand-binding RNAs have been enriched for by PCR in the cycles of affinity chromatography in the order of $10^{10}$-fold, ligand-regulated ribozymes present at much lower percentages would still be capable of isolation without undue experimentation. Those wells in which cleavage occurs in the presence or absence of the co-ligand would be PCR amplified and cloned and the transcripts of individual clones assayed for inactivation or activation by ligand.

The nature of the co-ligand can be chosen to be exogenously supplied, such as some non-toxic molecule which readily enters at least the target cells, or alternatively, an entirely endogenous system can be designed in which the controlling ligand is some small metabolite or macromolecule within the target cell which is directly or indirectly related to the pathology. For example, the protein encoded by the target RNA could be the ligand. The activity of the regulatable ribozyme is dependent on binding to the pathogenetic protein. As the level of target RNA falls due to cleavage by the ligand-activated ribozyme, the concentration of protein ligand falls. When the concentration falls below that at which the regulatable RNA molecules are all occupied, the rate of ribozyme cleavage will begin to fall off. By selecting for differing ribozyme:ligand affinities, the appropriate level of regulation of ribozyme-mediated destruction of the target RNA can be achieved for any given situation. For example, the pool of RNAs is subjected to affinity chromatography where the protein of interest is bound to the column. Ribozyme molecules which can bind the protein will remain on the column until eluted. Repeated rounds of PCR and chromatography enrich for ribozyme molecules which thus bind the protein. This population is then screened as described above to isolate molecules which are active ribozymes only in the presence of the ligand.

The present invention will be further understood with reference to the following non-limiting examples.

EXAMPLE 1: Detection of a short sequence corresponding to a portion of the Hepatitis B Virus Surface Antigen mRNA.

Figure 5A:
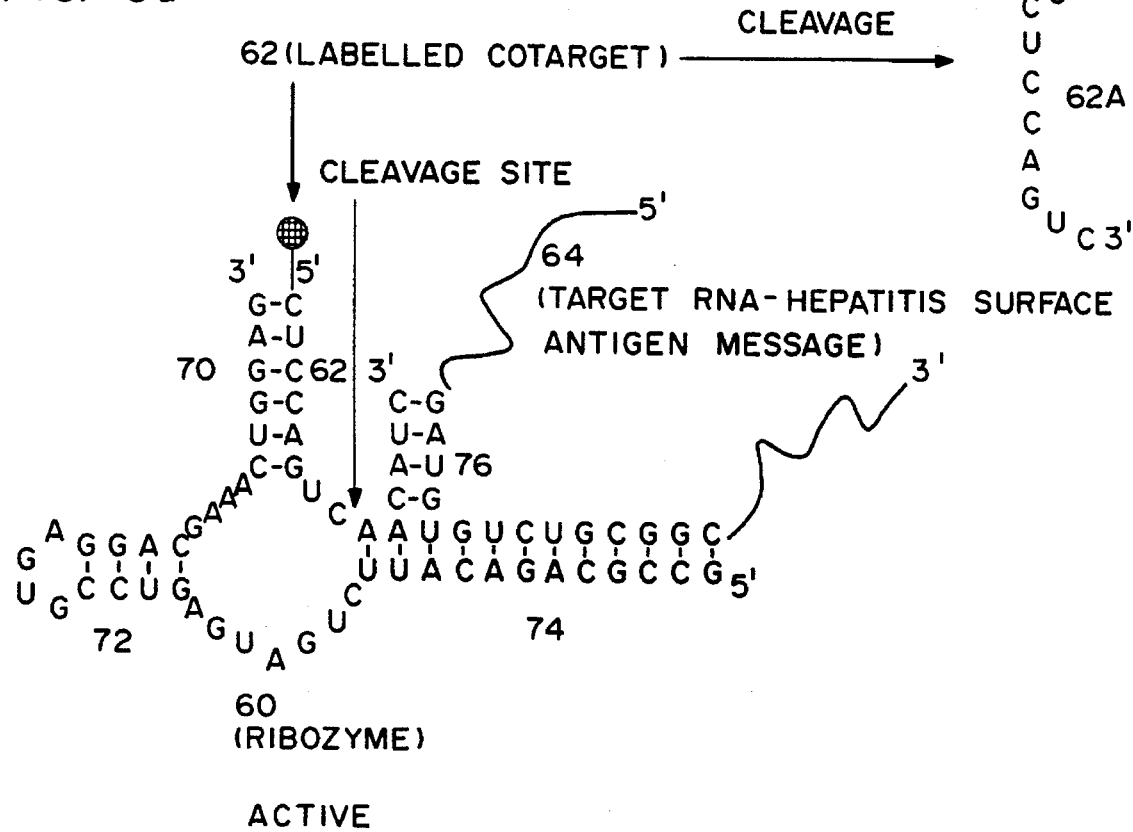
FIGS. 5A and 5B are schematics of an active ribozyme bound to co-target and target (FIG. 5A) and inactive ribozyme bound only to co-target (FIG. 5B).
Figure 5B:
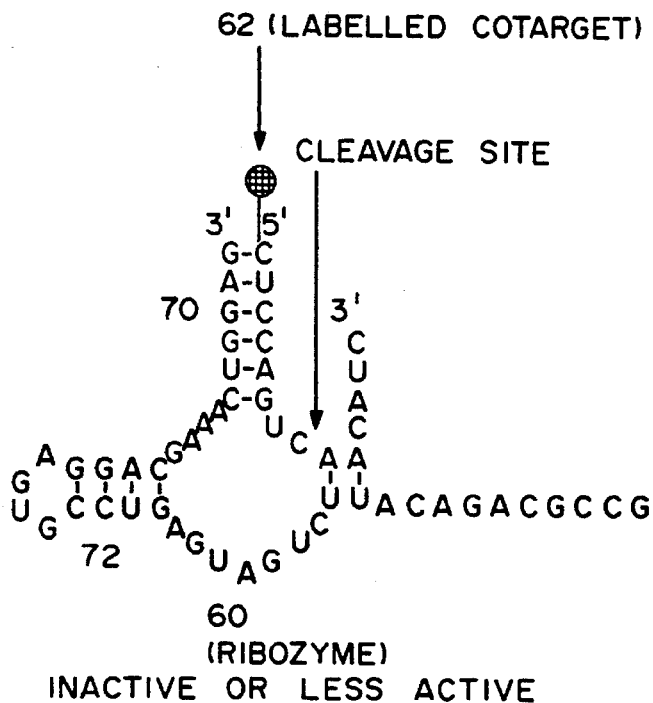

As shown in FIGS. 5A and 5B, based upon the structure of the hammerhead ribozyme, two constructs were designed, referred to as "ribozyme" 60 Sequence ID No. 1 and "co-target" 62 Sequence ID No. 2, such that in the presence of the disease target RNA 64, a trimolecular complex is formed consisting of stems A–D 70 Seq. ID No. 4, 72 Sequence ID No. 5, 72, 74, 76 Sequence ID No. 3. The resulting complex, shown in FIG. 5A, yields an active conformation of ribozyme and substrate, with subsequent cleavage of the co-target molecule 62 Sequence ID No. 2 and release of the labelled oligonucleotide 62a. In the absence of the disease target RNA 64, only stems A 70 Sequence ID No. 2 and B 72 Sequence ID No. 1 are formed completely; stem C 74 Sequence ID No. 1 consists of only two base pairs and is therefore insufficiently stable to support efficient cleavage of the co-target 62 Sequence ID No. 4, relative to the trimolecular complex.

Figure 6:
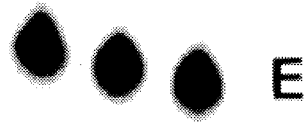
FIG. 6 is a 15% polyacrylamide/7M urea gel electrophoresed in 1× TBE at 800 volts. The reactions were performed in 50 mM Tris, 30 Mm Mg++, incubated for 2 hours at 37° C. Each component: enzyme (E), co-target (CT), and disease target (DT) were added at approximately equal specific activity. In lane 1, all three reactants are present but Mg++ is absent; in lane 2, all three reactants are present with Mg++; and in lane 3, only enzyme and co-target are present. The cleavage product (CP) can be seen in lane 2, and less so in lane 3.

FIG. 6 demonstrates the activity of the complete complex composed of ribozyme, co-target, and disease target, compared to that of a bimolecular complex of ribozyme and cotarget only. The disease target is a 20 nucleotide RNA corresponding to the hepatitis B virus surface antigen (HBsAg) mRNA. In lane 1, all three reactants are present but Mg++ is absent: no cleavage is observed. In lane 2, all three reactants are present with Mg++, and cleavage occurs. Importantly, as seen in lane 3 where the disease target is absent, the amount of cleavage of cotarget is clearly less than that in lane 2.

Example 2: Detection of a 800 nucleotide fragment corresponding to a portion of the Hepatitis B Virus Surface Antigen mRNA.

Figure 7A:
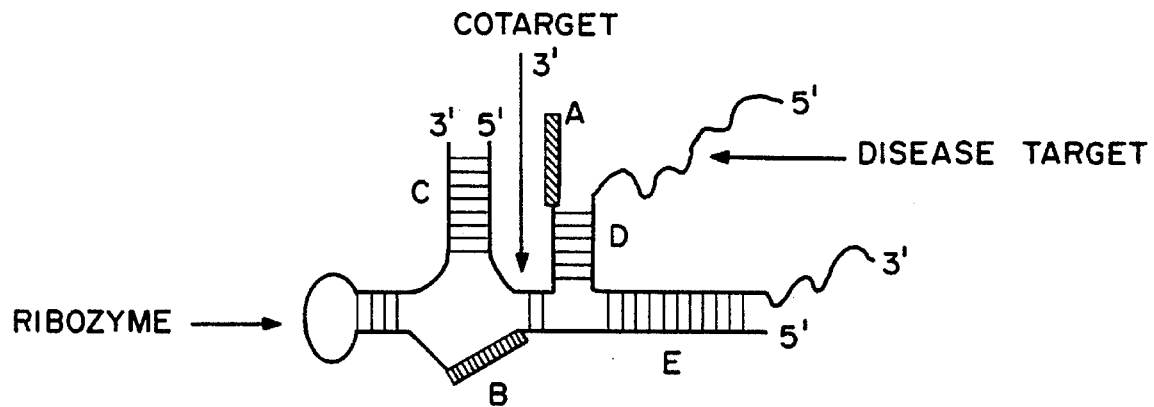
FIGS. 7A and 7B are schematics of a ribozyme/cotarget system which is much more active in the absence of the disease target than in its presence.
Figure 7B:
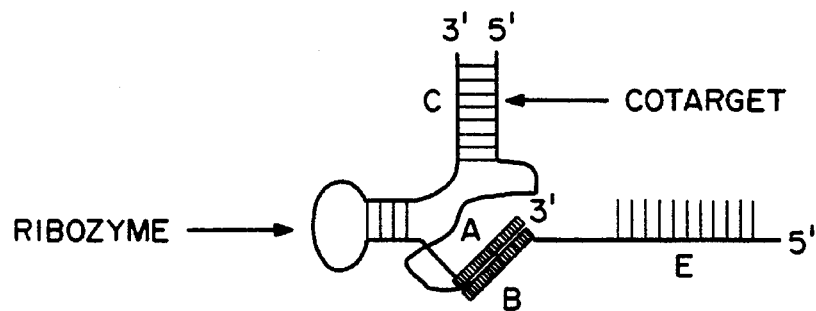

FIGS. 7A and 7B are schematics of a ribozyme which displays greater cleavage of the co-target in the absence of target than in the presence of target.

Figure 7C:
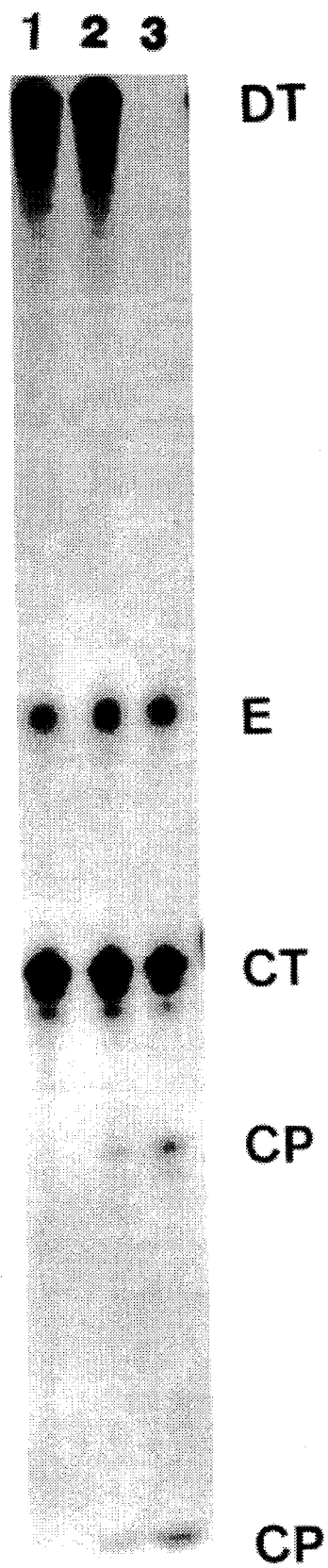
FIG. 7C is a 4% polyacrylamide/7 M urea gel electrophoresed at 800 V in 1× TBE. The reactants correspond to those in FIGS. 7A and 7B. The reaction was performed in 50 mM Tris with or without 30 mM Mg++ for 3 hrs at 37° C. The reactants were present at the following amounts: ribozyme., 7 pmoles; co-target (CT), 11.4 pmoles; disease target (DT), 0.37 pmoles.

The results in FIG. 7C demonstrate the effect of the ribozyme and cotarget in the presence or absence of disease target. When the HBV transcript is present, the ribozyme activity is less. This is exemplary of the method described herein where the presence of a molecule is detected by the increased release of label, presumably due to alternative base pairing.

As shown in FIG. 7C, in lane 1, all three reactants are present but Mg++ is absent: no cleavage is observed. In lane 2, all three reactants are present with Mg++, and cleavage occurs. Importantly, as seen in lane 3 where the disease target is absent, the amount of cleavage of cotarget is clearly much greater than that in lane 2.

Modifications and variations of the method and compositions of the present invention will be obvious to those skilled in the art from the foregoing detailed description. Such modifications and variations are intended to come within the scope of the following claims.

We claim:

1. A method for detecting a target nucleic acid molecule in a solution, comprising:

providing in the solution under conditions wherein two complementary nucleotide molecules will hybridize, a ribozyme molecule, a labelled co-target nucleic acid molecule and the target nucleic acid molecule, wherein the co-target and the target molecules have different sequences and wherein the ribozyme molecule comprises two regions complementary to portions of the co-target and target nucleic acid molecules, wherein the first portion is present on the labelled co-target nucleic acid molecule which contains a cleavage site for the ribozyme and the second portion is present on the target nucleic acid molecule, wherein the complementary regions include at least the minimum number of complementary nucleotides to obtain hybridization between the ribozyme molecule and the co-target and target nucleic acid molecules, allowing the ribozyme molecule to react with the labelled co-target nucleic acid molecule and the target nucleic acid molecule, and detecting the presence of free label when the target nucleic acid molecule is present in solution as compared with when the target nucleic acid molecule is not present in solution.

2. The method of claim 1 wherein the ribozyme is derived from the group consisting of *Tetrahymena* ribozymes, RNAase P, ribozymes derived from newt satellite ribozyme, hammerhead ribozymes derived from plant viroids, and axehead ribozymes derived from hepatitis delta virus.

3. The method of claim 1 wherein the target nucleic acid molecule hybridizes with the labelled co-target nucleic acid molecule.

4. The method of claim 3 wherein the target nucleic acid molecule encodes a protein.

5. The method of claim 1 wherein the labelled cotarget nucleic acid molecule is immobilized on a solid support.

6. The method of claim 1 wherein the labelled co-target nucleic acid molecule is labelled with a label selected from the group consisting of dyes, enzymes reactive with a chromogenic substrate, fluorescent labels, chemiluminescent labels, and radioactive labels.

7. The method of claim 1 wherein the ribozyme is conformationally active when the ribozyme hybridizes to the target nucleic acid molecule.

8. The method of claim 1 wherein the ribozyme is conformationally active when the ribozyme is hybridized to both the target nucleic acid molecule and the labelled co-target nucleic acid molecule.

9. The method of claim 1 wherein the ribozyme is stable to elevated temperatures in excess of 37° C. and the target nucleic acid molecule hybridizes to the ribozyme at a temperature in excess of 37° C.

10. The method of claim 1 wherein when the target nucleic acid molecule hybridizes to the ribozyme molecule there is less label detected than when the target nucleic acid is not hybridized to the ribozyme molecule.

11. The method of claim 1 wherein when the target nucleic acid molecule hybridizes to the ribozyme there is more label detected than when the target nucleic acid is not hybridized to the ribozyme molecule.

12. A kit for use in the method of claim 1 comprising a ribozyme molecule, a co-target nucleic acid molecule which contains a cleavage site for the ribozyme, and a target nucleic acid molecule, wherein the co-target and target molecules have different sequences, and wherein the ribozyme comprises two regions complementary to portions of the co-target and target nucleic acid molecules, wherein the first portion is present on the co-target nucleic acid molecule and is complementary to a first region of the ribozyme and the second portion is present on the target nucleic acid molecule and is complementary to a second region of the ribozyme, wherein the complementary regions of the ribozyme include at least the minimum number of complementary nucleotides to obtain hybridization between the ribozyme molecule and the first portion on the co-target and the second portion on the target molecule.

13. The kit of claim 12 wherein the co-target nucleic acid molecule hybridizes to the target nucleic acid molecule.

14. The kit of claim 12 wherein the co-target nucleic acid molecule is labelled.

15. The kit of claim 12 wherein the target nucleic acid molecule encodes a protein.

16. The kit of claim 12 wherein the ribozyme is derived from the group consisting of *Tetrahymena* ribozymes, RNAase P, newt satellite ribozyme, hammerhead ribozymes derived from plant viroids, and axehead ribozymes derived from hepatitis delta virus.

17. The kit of claim 12 wherein the ribozyme is conformationally active when hybridized the first portion of the first molecule.

18. The kit of claim 12 wherein the ribozyme is conformationally active when the first complementary region is hybridized to the first portion on the co-target molecule and the second complementary region is hybridized to the second portion on the target molecule.

19. The kit of claim 12 wherein the enzymatic activity of the ribozyme is altered by binding of a regulating molecule to the ribozyme.

20. The kit of claim 12 wherein the ribozyme is conformationally active at a temperature between 37° and 60°.

21. The kit of claim 14 wherein the labelled co-target nucleic acid molecule is immobilized on a solid support.

22. The kit of claim 14 wherein the labelled co-target nucleic acid is labelled with a label selected from the group consisting of dyes, enzymes reactive with a chromogenic substrate, fluorescent labels, chemiluminescent labels, and radioactive labels.

23. The kit of claim 14 wherein when the target nucleic acid is hybridized to either the ribozyme or the co-target molecule there is less label detected than when the target nucleic acid molecule is not hybridized to either the ribozyme or the co-target molecule.

24. The kit of claim 14 wherein when the target nucleic acid molecule is hybridized to either the ribozyme or the co-target molecule there is more label detected than when the target nucleic acid molecule is not hybridized to either the ribozyme or the co-target molecule.

25. A method for detecting a targeted nucleic acid molecule in a solution, comprising:

adding to the solution a trans-acting ribozyme labelled with a label selected from the group consisting of dyes, enzymes reactive with a chromogenic substrate, fluorescent labels, chemiluminescent labels, and radioactive labels, and having two regions of complementarity to the targeted nucleic acid molecule, wherein the label is cleaved from the ribozyme when the ribozyme hybridizes to the targeted molecule; and detecting the targeted molecule by detecting the label cleaved from the ribozyme.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Synthetic ( i x ) FEATURE:
        ( A ) NAME/KEY: misc_RNA
        ( B ) LOCATION: 1..41
        ( D ) OTHER INFORMATION: /note="Active Ribozyme"

( x i ) SEQUENCE DESCRIPTION: SEQ ID NO:1:

```
GCCGCAGACA  UUCUGAUGAG  UCCGUGAGGA  CGAAACUGGA  G                    4 1
```

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Synthetic ( i x ) FEATURE:
        ( A ) NAME/KEY: misc_RNA
        ( B ) LOCATION: 1..14
        ( D ) OTHER INFORMATION: /note="Bonded cotarget"

( i x ) FEATURE:

5,589,332

13

-continued

14

( A ) NAME/KEY: misc_feature
        ( B ) LOCATION: 8..9
        ( D ) OTHER INFORMATION: /note="Cleavage site"

( x i ) SEQUENCE DESCRIPTION: SEQ ID NO:2:

CUCCAGUCAA CAUC                                                                14

( 2 ) INFORMATION FOR SEQ ID NO:3:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: unknown ( i i ) MOLECULE TYPE: RNA (genomic)

( i i i ) HYPOTHETICAL: NO ( i v ) ANTI-SENSE: NO ( v i ) ORIGINAL SOURCE:
                ( A ) ORGANISM: Hepatitus B Virus ( i x ) FEATURE:
                ( A ) NAME/KEY: misc_feature
                ( B ) LOCATION: 1..14
                ( D ) OTHER INFORMATION: /note="Target RNA-hepatitis
                    surface antigen message"

( x i ) SEQUENCE DESCRIPTION: SEQ ID NO:3:

GAUGUGUCUG CGGC                                                                14

( 2 ) INFORMATION FOR SEQ ID NO:4:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
                ( A ) ORGANISM: Synthetic ( i x ) FEATURE:
                ( A ) NAME/KEY: misc_RNA
                ( B ) LOCATION: 1..14
                ( D ) OTHER INFORMATION: /note="Labelled cotarget"

( x i ) SEQUENCE DESCRIPTION: SEQ ID NO:4:

CUCCAGUCAA CAUC                                                                14

( 2 ) INFORMATION FOR SEQ ID NO:5:

( i ) SEQUENCE CHARACTERISTICS:
                ( A ) LENGTH: 41 base pairs
                ( B ) TYPE: nucleic acid
                ( C ) STRANDEDNESS: single
                ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
                ( A ) ORGANISM: Viroid (Plant)

(ix) FEATURE:
    (A) NAME/KEY: misc_feature
    (B) LOCATION: 1..41
    (D) OTHER INFORMATION: /note="Inactive Ribozyme"

(xi) SEQUENCE DESCRIPTION: SEQ ID NO:5:

GCCGCAGACA UUCUGAUGAG UCCGUGAGGA CGAAACUGGA G    41